United States Patent [19]

Halpern

[11] Patent Number: 5,133,766
[45] Date of Patent: Jul. 28, 1992

[54] FEMORAL HEAD REMODELING AND FEMORAL INSERT AND DRILLING AID THEREFOR

[76] Inventor: Alan A. Halpern, 1400 Low Rd., Kalamazoo, Mich. 49008

[21] Appl. No.: 663,717

[22] Filed: Mar. 4, 1991

[51] Int. Cl.$^5$ ............................................. A61F 2/36
[52] U.S. Cl. .................................... 623/23; 606/89; 606/87
[58] Field of Search .................. 606/86–87, 606/89, 65, 67; 623/23, 22

[56] References Cited

U.S. PATENT DOCUMENTS

| | | | |
|---|---|---|---|
| 3,965,490 | 6/1976 | Murray et al. | 623/23 |
| 4,068,324 | 1/1978 | Townley et al. | 623/23 |
| 4,292,695 | 10/1981 | Koeneman | 623/22 X |
| 4,532,661 | 8/1985 | Halpern | 623/23 |
| 4,670,015 | 6/1987 | Freeman | 623/23 |
| 4,704,686 | 11/1987 | Aldinger | 623/22 X |
| 4,978,359 | 12/1990 | Wilhelm et al. | 623/23 |

FOREIGN PATENT DOCUMENTS

| | | | |
|---|---|---|---|
| 2600527 | 12/1987 | France | 623/22 |
| 2203943 | 11/1988 | United Kingdom | 623/22 |

Primary Examiner—Randall L. Green
Assistant Examiner—D. Willse
Attorney, Agent, or Firm—Gordon W. Hueschen

[57] ABSTRACT

An improved femoral hip joint replacement and method are disclosed, as well as a drilling fixture to assist with carrying out the method. The method involves the provision of an elongated excavation or aperture by drilling of overlapping boreholes in the top of the femoral head, and then securing therein a similarly-contoured femoral insert adapted to be located within the femoral shaft and within the boreholes in the remaining upstanding portions of the remodeled femoral head. A metal cap, of approximately the normal femoral head size, or an arcuate portion thereof, is secured to or integral with the insert and projects in usual manner from the superior portion of the remodeled femoral head and is adapted to fit into an acetabulum of the hipbone. According to the method of the invention and with the employment of the femoral hip joint replacement provided thereby, there is substantially no chance of axial or rotational movement of the femoral hip joint replacement or any portion thereof within the femoral shaft or with respect to the remoldeled femoral head, and the remodeled femoral head produced according to the invention and employing the femoral hip joint prosthesis of the invention is accordingly characterized by superior load-bearing characteristics and stability in operation.

40 Claims, 5 Drawing Sheets

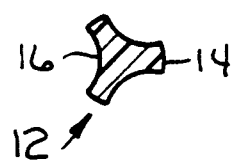
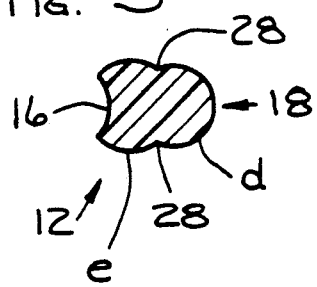
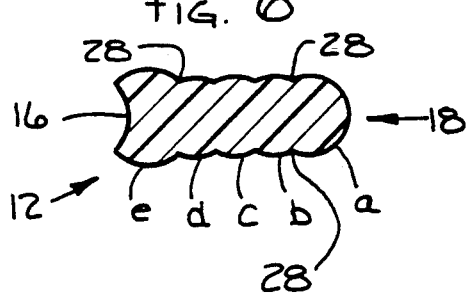
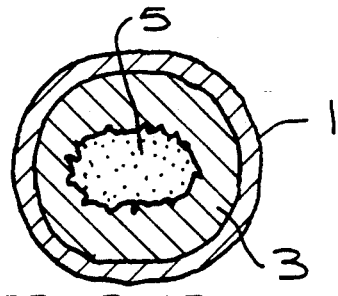
PRIOR ART
Fig. 7
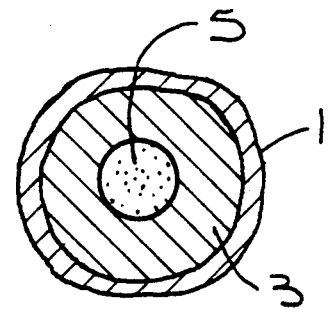
Fig. 8
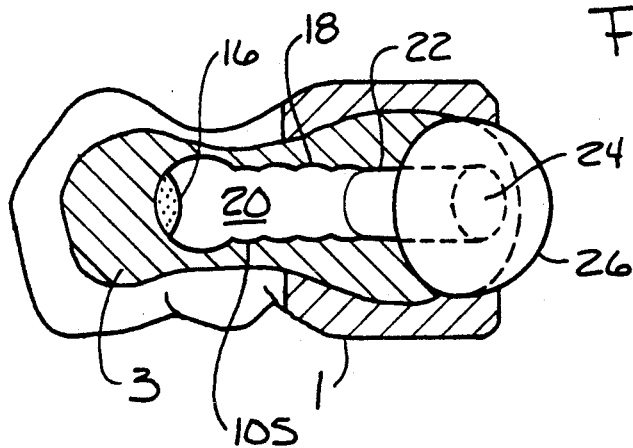
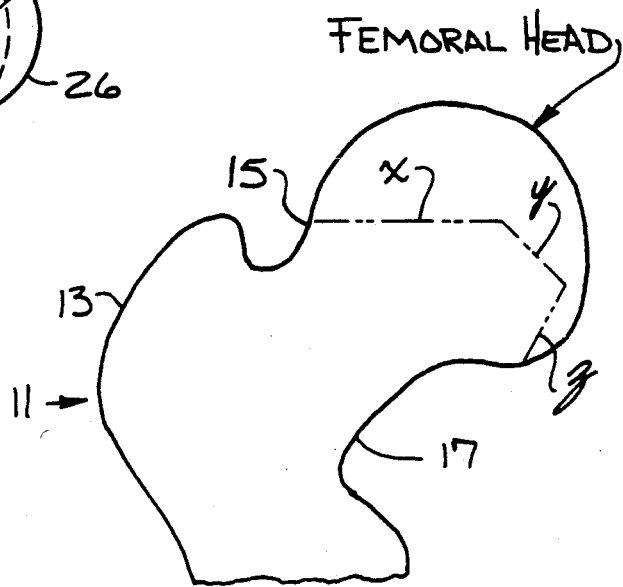

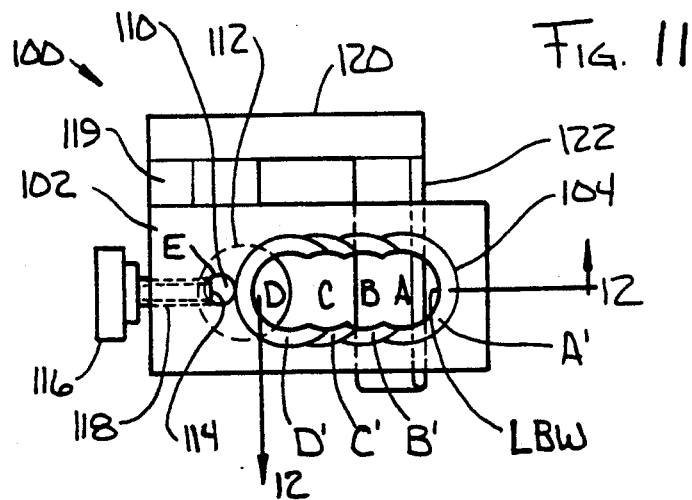
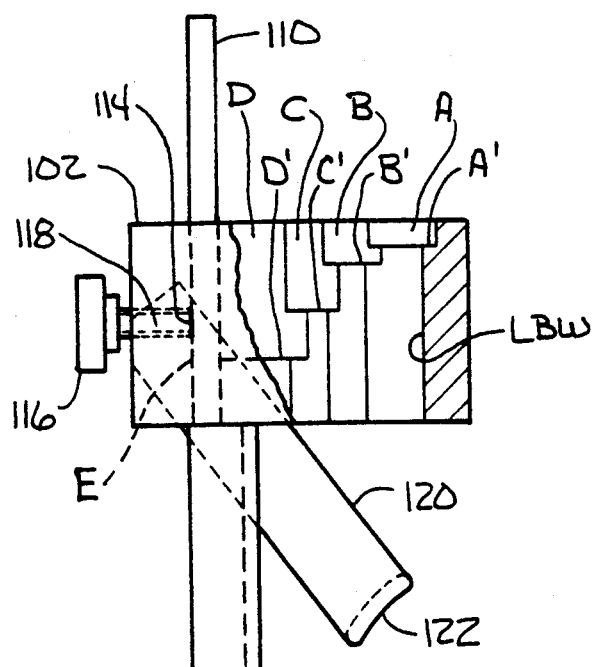
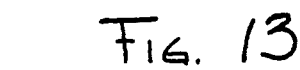
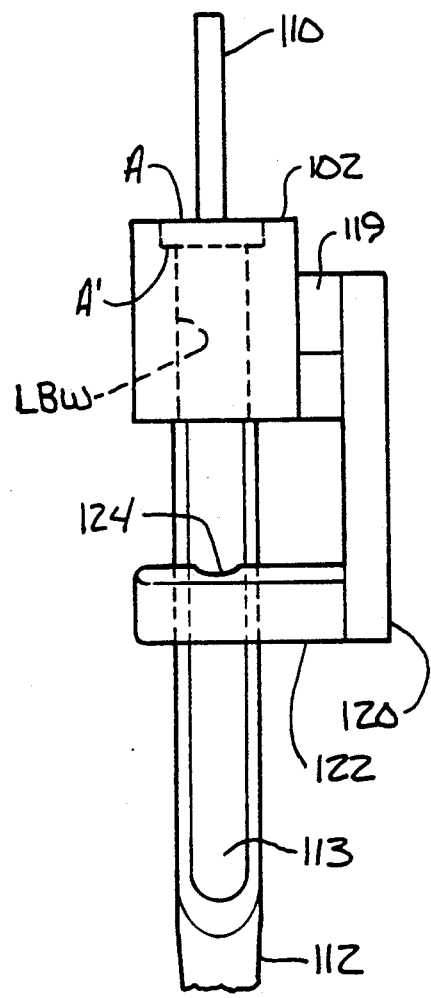

FEMORAL HEAD REMODELING AND FEMORAL INSERT AND DRILLING AID THEREFOR

BACKGROUND OF THE INVENTION

1. Field of Invention

This invention relates to a novel method for remodeling of the femoral head and to prosthetic means, including an intramedullary insert and attached or integral shell or cap, for use as a part of the said femoral head remodeling procedure, and to a drilling fixture for use in carrying out the method.

The ultimate product of the present invention may be employed with an intact acetabulum, namely, the cup-shaped socket in the hip bone, or in combination with prosthetic acetabular sockets or cups, which are widely available from orthopaedic supply organizations today and which are well known in the art. A representative prosthetic acetabular socket is disclosed in U.S. Pat. No. 3,722,002. Representative orthopaedic supply houses specializing in prosthetic acetabular sockets include DePuy, Howmedica, and Zimmer.

As is well known in the art, the hip joint comprises the acetabula or an acetabular prosthesis, which is a cup-shaped socket in the hip bone, providing a generally hemispheric surface, within which the femoral head, having a corresponding generally hemispheric surface contour, rotates by means of a thin layer of cartilage under normal conditions and on a thin layer of plastic or the like under conditions of reconstruction and prosthesis after the normal cartilage has become eroded or the hip joint has become otherwise inoperative due to aging, injury, or other abnormal condition arising from any of a multitude of etiologies.

The ultimate product of the present invention, which is a femur having a remodeled femoral head including prosthetic means comprising the intramedullary insert and its integral or attached cap, is intended for use in cooperation with a normal or prosthetic acetabular socket, but the provision of such acetabular socket does not constitute a part of the present invention.

Reference is made to my previous U.S. Pat. No. 4,532,661, issued Aug. 6, 1985, entitled "Femoral Head Remodeling and Prosthetic Means Therefor" and to U.S. Pat. No. 4,670,015, issued Jun. 2, 1987 to Freeman and entitled "Hip Implant", the disclosures of which prior patents are referred to herein and by reference made a part hereof. In the opinion of the present inventor, the developments of these two (2) patents are at the cutting edge of technology in the hip implant and femoral insert technology and methodology.

2. Prior Art

The prior art is replete with procedure and prosthetic means for remodeling of the femoral head. This is well documented in my previous U.S. Pat. No. 4,532,661 of Aug. 6, 1985, to which reference is now made and the entire disclosure of which is incorporated herein by reference.

Another recently-issued U.S. Patent to which reference is made is the aforesaid Freeman U.S. Pat. No. 4,670,015 of Jun. 2, 1987, which provides a somewhat more simplified version of a prosthetic means, comprising an intramedullary insert with an integral cap, than disclosed in my previous U.S. Pat. No. 4,532,661, upon either of which prior art devices, and methods which employ the same, the present invention is a highly-advantageous and valuable improvement, although relatively simple in its nature and approach, providing superior load-bearing characteristics and stability in use or operation.

OBJECTS OF THE INVENTION

It is an object of the present invention to provide a novel method for remodeling of the femoral head comprising the provision of an elongated excavation or aperture in the superior neck by the drilling of overlapping cylindrical boreholes of different depths therein, a drilling fixture to assist in carrying out the said method, and a unique femoral or intramedullary insert of dimensions corresponding to the said excavation or aperture, thereby to impart superior load-bearing characteristics and stability during use of the prosthesis. Additional objects will become apparent as the description proceeds and still other objects will be readily apparent to one skilled in the art.

SUMMARY OF THE INVENTION

My invention then comprises, inter alia, the following, singly or in combination:

A femoral insert, adapted to be secured in a femoral shaft as part of a femoral hip joint replacement, comprising an elongated vertical shaft portion with a longitudinal axis generally corresponding to the vertical axis of a femoral shaft, and a wedge-shaped portion extending from the shaft portion at or near the top thereof and constituting an offset to the longitudinal axis of said vertical shaft, said wedge-shaped portion terminating in a stem portion adapted to be capped by a femoral cap or shell, said vertical shaft and offset wedge-shaped portions having a configuration, when viewed from the top of said insert, comprising a plurality of overlapping circles, with inwardly-extending indentations at the intersections of circumferences of the circles, side surfaces of said wedge-shaped-offset portion comprising a plurality of adjoining convexly-arcuate surface segments defining the exteriors of a plurality of vertically-arranged overlapping cylindrical segments, the bottoms of which cylindrical segments are stepped due to being located at progressively greater distances from the top of said insert beginning adjacent said stem portion and progressing toward said vertical shaft portion; such a femoral insert wherein said insert is adapted to provide secure engagement within a correspondingly-shaped aperture in a resected femoral head and to provide contact or close proximity of the stepped bottom of said wedge-shaped portion with the cortex of said resected femoral head at the inferior neck thereof; such a femoral insert comprising also a femoral cap or shell in place on said stem; such a femoral insert wherein at least the bottom of said vertical shaft is flanged; such a femoral insert wherein said vertical shaft is multi-flanged or tri-flanged; such an insert wherein the vertical shaft is tri-flanged and an arcuate groove distal to the stem portion extends to the top of the shaft; such an insert wherein the number of cylindrical segments is less than six (6); such a femoral insert wherein said shaft and said wedge-shaped offset comprise five (5) cylindrical sections; such an insert having five (5) cylindrical segments including an at least partial cylindrical segment at the top of the vertical shaft; such an insert wherein one cylindrical segment has a larger circumference than other segments; such an insert having a top surface which is substantially planar; such an insert in place in a resected and correspondingly excavated femur; such a femoral insert in place in a resected femur comprising a femur having an excavated femoral shaft and an allograft secured in place therein, said allograft having been pre-drilled to provide an aperture corresponding to a complementary configuration of the insert; and such a femoral insert in place in a resected and correspondingly excavated femur having an excavated femoral shaft and an allograft secured in place therein, said allograft having been drilled-in-place to provide an aperture corresponding to a complementary configuration of the insert.

Moreover, a method of preparing an aperture in a femur for insertion of a complentarily-shaped femoral insert thereinto, comprising the steps of providing an elongated excavation or aperture within the femoral shaft generally corresponding to the shaft of a femoral insert to be inserted therein and essentially in line with the vertical axis of said femoral shaft by drilling or routing a borehole into the same, providing an elongated aperture in the superior neck of said femur by drilling a plurality of cylindrical boreholes vertically downwardly into the superior neck between the end portion thereof distal to the femoral shaft and the portion thereof proximal to said femoral shaft, arranging said drilling to provide said boreholes with overlapping circumferences and thereby also to provide inwardly-extending protuberances at the intersections of said overlapping circumferences, extending said boreholes downwardly into said superior neck to different depths so as to bring them essentially into contact with or close proximity to the cortex of the femur at about the inferior neck and at progressively greater depths beginning at the portion of the superior neck distal to said femoral shaft and progressing toward the portion proximal to said femoral shaft, thereby to provide an elongated excavation comprising a plurality of overlapping cylindrical boreholes in said superior neck suitable for the close-fitting insertion of a femoral insert having an essentially corresponding configuration thereinto; such a method including the step of resecting the femoral head to provide a substantially planar and extended surface to the superior neck; such a method wherein the number of cylindrical boreholes drilled is less than six (6); such a method wherein a total of five (5) boreholes is provided; such a method wherein five (5) cylindrical boreholes are drilling including a cylindrical borehole in the femoral shaft; such a method wherein one cylindrical borehole has a larger circumference than other boreholes; such a method wherein the borehole drilled in said femoral shaft has a greater circumference than other boreholes; such a method wherein a femoral insert having a substantially planar top surface and complementary contour and cross-section is thereafter press-fit therein without the aid of surgical cement; such a method when applied to a resected femur comprising an allograft secured in place therein; such a method when applied to the femoral shaft of a resected femur and to an allograft comprising a superior neck, which allograft is thereafter secured in place in said femur; such a method wherein the successive drillings are facilitated by the employment of a drilling fixture comprising elongated means adapted to fit into an excavated intramedullary canal of a femur and surmounted by mounting means, a body member mounted on said mounting means, means for adjusting said body member vertically and angularly upon said mounting means and for securing said body member in a predetermined position with respect to said mounting means and said femur, said body member comprising a plurality of boreholes, each with its respective stop means, adapted to cooperate with a drill bit comprising complementary stop means, for drilling cylindrical openings in the resected head of said femur to different depths, depending upon the position at which the stop means is located for a particular borehole provided in the body member of said fixture; and such a method wherein the successive drillings are facilitated by the employment of a drilling fixture comprising an elongated vertical shaft adapted to fit into an excavated intramedullary canal of a femur and surmounted by a vertical rod, a body member mounted on said rod and adjustable vertically and angularly upon said rod and securable in a predetermined position on said rod, said body member comprising a plurality of boreholes, each with its respective stop flange, adapted to cooperate with a drill bit comprising a complementary flange, for drilling cylindrical openings in the resected head of said femur to different depths, depending upon the position at which the stop flange is located for a particular borehole provided in the body member of said fixture.

Moreover, a drilling fixture or jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein, said boreholes comprising overlapping circumferences and each borehole being provided with stop means therefor, the said stop means for said plurality of boreholes being located at different heights for different boreholes, elongated means adapted to be inserted into an excavated femoral shaft, the position of said stop means, for said boreholes in said body member, being progressively vertically lower starting at a borehole which is distal to said elongated means and progressing toward a borehole which is proximal to said elongated means, and means for mounting and for releasably adjusting and securing said drilling fixture or jig both vertically and angularly atop the upper surface of the femur once said elongated means is in place in the borehole of said femoral shaft.

And further, a drilling fixture or jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein,. said boreholes comprising overlapping circumferences and each borehole being provided with a stop flange therefor, the said stop flanges for said plurality of boreholes being located at different heights for different boreholes, an elongated vertical shaft having a vertical axis, corresponding essentially to the vertical axis of a starting femoral shaft, having an elongated vertical borehole drilled therein, and adapted to be inserted thereinto, the position of said stop flanges, for said boreholes in said body member, being progressively vertically lower starting at a borehole which is distal to said vertical shaft and progressing toward a borehole which is proximal to said vertical shaft, and means for releasably adjusting and securing said drilling fixture or jig both vertically and angularly atop an upper surface of the femur once said elongated vertical shaft is in place in the borehole of said femoral shaft; such a drilling fixture or jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein, said boreholes comprising overlapping circumferences and each borehole being provided with a stop flange therefor, the said stop flanges for said plurality of boreholes being located at different heights for different boreholes, a separate vertical aperture in said body member which is spaced from said boreholes and adapted to receive mounting rod means therein, an elongated vertical shaft having a vertical axis corresponding essentially to the vertical axis of a femoral shaft having an elongated vertical borehole drilled therein, and adapted to be inserted thereinto, mounting rod means surmounting said vertical shaft and adapted to be inserted into said separate vertical aperture in said body member, securing means for adjusting the height of said body member upon said mounting rod means and maintaining it at a predetermined height thereon, the position of said stop flanges, for said boreholes in said body member, being progressively vertically lower starting at a borehole which is distal to said mounting rod means and progressing toward a borehole which is proximal to said mounting rod means, and further releasable securement means for releasably securing said drilling fixture or jig in place atop an upper surface of a femur once said elongated vertical shaft is in place in the borehole of said femoral shaft and said body member is in place and releasably secured on said mounting rod means; such a drilling fixture wherein said body member is also rotatable on said mounting rod means; such a drilling fixture wherein said securing means comprises threaded screw means and corresponding threads in said body member; such a drilling fixture wherein said mounting rod means comprises a flat portion for engagement by said screw means to minimize undesired rotation thereof and to assist in fixing said body member at a proper angle both with respect to said mounting rod means and with respect to the femur being drilled; such a drilling fixture wherein said elongated vertical shaft has an arcuate recess or groove along the length thereof facing the borehole in said body member most proximal thereto for enabling a drill bit to be placed in said proximal borehole without engaging said shaft; such a drilling fixture wherein said further releasable securement means comprises an arm attached to said body member at an angle and a cross member adapted to engage the outer surface of a femur being drilled at about the inferior neck thereof; such a drilling fixture comprising also a drill bit having a drill stem and a drill head, said drill head providing a flange for engagement with said stop flanges, provided for said boreholes in said body member, and having a drill bit length below said flange which is calculated to permit said drill bit to drill into the superior neck of the femur being drilled to a point in contact with or closely adjacent to the cortex of the femur at about the inferior neck thereof; such a drilling fixture including a stabilizing plug for insertion into a first borehole in said femur, once it has been completed, through the corresponding borehole provided in said body member of said drilling fixture to further stabilize the drilling fixture upon the femur; and finally such a drilling fixture wherein said body member has a substantially planar lower surface for lying flat in contact with or in close proximity to a substantially planar superior surface of a flattened and extended superior neck of a femur being drilled.

BRIEF DESCRIPTION OF THE DRAWINGS

In the drawings:

FIGS. 4, 5, and 6 are cross-sectional views through the femoral insert of FIG. 3, taken along the lines 4—4, 5—5, and 6—6 of FIG. 3.

FIG. 8 is a cross section taken along the line 8—8 in FIG. 1 without the presence of the intramedullary insert, whereas FIG. 7 is a cross section taken along approximately the same line in a femur, the intramedullary canal of which is reamed or rasped out according to prior art procedure.

FIG. 7 is thus a cross-sectional view of a femur, taken below the lesser trochanter, showing the irregular aperture produced when a rasp or reamer is employed according to prior art procedure for removal of cancellous bone tissue from the femoral shaft, and FIG. 8 is a cross-sectional view taken at approximately the same place as FIG. 7, showing the precise and regular nature of the aperture produced when the cancellous bone is removed by drilling or routing rather than the normal rasping or reaming.

FIG. 9 is a top view of the assembly of FIG. 1, showing the femoral insert in place in an elongated aperture provided therefor in the femur and the femoral cap or shell in place on the stem of the femoral insert.

FIG. 10 is a side view of the upper portion of a femur, including the head, superior neck, calcar, and greater trochanter, illustrating in phantom lines the manner in which the femoral head may be resected in accord with the present invention.

FIG. 11 is a top view of a drilling fixture, guide, or jig which is especially useful in carrying out the method of the present invention.

FIG. 12 is a side view, partially broken away along lines 12—12, of the drilling fixture of FIG. 11, including adjusting and securing members for temporarily securing the fixture in position and to the femoral head during use.

FIG. 13 is a front view of the drilling fixture of FIG. 12, showing an optional but preferred groove in the clamping member for centering of the fixture on the femur at approximately the calcar.

DETAILED DESCRIPTION OF THE INVENTION

In usual methodology for total or partial hip joint replacement, following dislocation of the hip joint, virtually the entire neck of the femur is removed. In my approach, the minimum amount of bone is removed from the surface of the head of the femur to expose healthy, firm bone surfaces, whereafter the prosthetic femoral insert is placed into position and secured in such position to provide a replacement hip joint surface, ordinarily of metal, having the configuration of a ball (i.e., the femoral head) of substantially the same size and in substantially the same location as the original ball, whereafter the recapped femur and the acetabulum or acetabulum socket member are relocated in rotatable engagement with one another.

Figures 1, 2, 3:
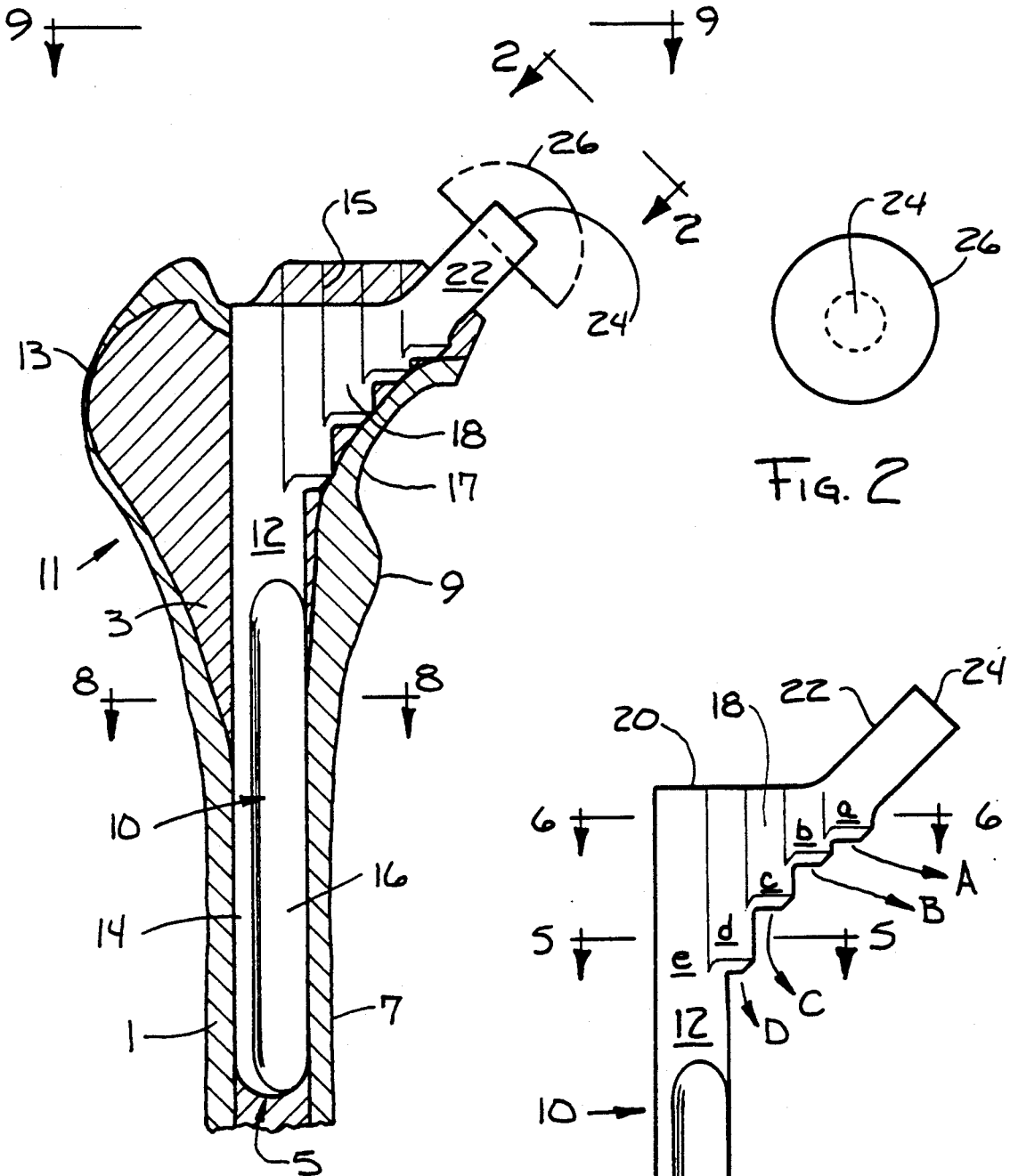
FIG. 1 is a side view of a femoral insert of the invention in place in the upper portion of a femur having a resected femoral head, the portions of the femur shown in the Figure being shown in cross section, and including the resected femoral head, the greater trochanter, the lesser trochanter, the calcar, cancellous bone interior of the cortex, and the femoral shaft running vertically in the Figure, in which vertical shaft the femoral insert of the invention is inserted after removal of cancellous bone therefrom, a femoral cap or shell being shown press-fit in place over the stem of the femoral insert.
FIG. 2 is a top or front view of the femoral cap or shell with the stem of the femoral insert, to which it is attached, being shown in shadow lines.
FIG. 3 is a more detailed side view of the femoral insert of the invention.

Referring now more particularly to the drawings for a better understanding of the invention, wherein the same numbers are used to refer to the same elements or members throughout:

From FIG. 1 is seen the upper portion of the femur 11 including the greater trochanter 13, the lesser trochanter 9, the calcar or inferior neck 17, the femoral shaft 7 with its outer layer of hardened bone or cortex 1 and its inner layer of softer or cancellous bone 3, with cancellous bone removed from the intramedullary canal 5, i.e., from the interior of the femoral shaft 7, wherein it is replaced by the lower grooved portion of the vertical stem or shaft 12 of the femoral insert 10, provided with a plurality of ridges 14 and a plurality of arcuate or other grooves 16, advantageously three of each, for intimate contact of the lower portion of vertical stem or shaft 12 with the excavated interior 5 of the femoral shaft 7. At the top of the femur 11 is the resected femoral head, resected generally along the lines indicated in FIG. 10, to produce a flattened and extended superior neck 15. At the upper reach of vertical shaft or stem 12 of the femoral insert 10 is a wedge-shaped portion 18 which extends laterally from the vertical stem 12 at or near the top end thereof. The wedge-shaped portion 18 terminates in proximal stem 24, having a circular or other suitable cross section, to which is press-fit femoral cap or shell 26 by means of a suitable correspondingly-dimensioned aperture therein.

As will be seen from FIG. 1, the wedge-shaped portion 18 does not have a flat or even exterior surface, but is provided with a series of arcuate convex bulges and indentations therein, better seen from FIG. 3 and particularly from the cross sectional view of FIGS. 5, 6, and 9, and may be described as a series of cylindrical segments having overlapping circumferences and different lengths. According to the invention, this external surface configuration is provided to correspond with an identical or nearly identical configuration of an elongated aperture 105 (see FIG. 9) in the top of the femur into which the insert 10 is adapted to be placed, the configuration of the corresponding aperture 105 being provided by drilling or routing a plurality of circumferentially-overlapping boreholes vertically-downwardly to different depths into the resected head of the femur, thereby providing a plurality or succession of vertical apertures in the resected superior neck 15 which, because of their overlapping nature, merge to provide the single extended or elongated aperture 105 into which the corresponding wedge-shaped portion 18 of the femoral insert 10 fits snugly and rigidly in practice. Although, as shown, the upper surface of insert 10 is slightly below the flattened and extended relatively planar surface of superior neck 15, in practice it is equally satisfactory, and sometimes even advantageous, for the upper surface of insert 10 to be approximately even with or slightly above the upper relatively planar surface of superior neck 15 of the resected femur.

As seen from FIGS. 1 and 3, the femoral insert 10 comprises vertical stem 12 having, at its bottom reaches, a series of ridges 14 and grooves 16, which provide a flanged cross section, usually a tri-flanged cross section as shown in FIG. 4. Also seen are wedge-shaped portion 18 at the upper end of stem 12, the insert preferably having a substantially flat or horizontal planar surface 20 at the uppermost end thereof, and, at the extreme outer end of wedge-shaped or right-handed offset portion 18, proximal stem 26 having a circular cross section at the end thereof for engagement with the femoral cap or shell 26 as previously described.

When in place in the resected and excavated femur, as shown in FIG. 1, the vertical stem portion 12 of insert 10 corresponds essentially with the area excavated from the interior 5 of the femoral shaft 7, and the wedge-shaped or right-handed offset portion 18 fits snugly into the elongated aperture 105 in the extended superior neck 15 resulting from a series or plurality of overlapping cylindrical excavations provided by drilling or routing thereof as will be described further hereinafter.

As shown in FIG. 1, the wedge-shaped portion 18 of insert 10 fits and seats within an elongated aperture 105 provided at the top of the resected femur, and this offset portion 18 of insert 10 is designed and adapted to seat upon the remaining cortex at approximately the inferior neck or calcar 17 thereof, as well as at other points higher and lower on the femoral cortex, as clearly shown in FIG. 1.

As further shown in FIG. 3, this right-handed offset or wedge-shaped portion 18 of the femoral insert 10 is provided with a series of cylindrically-shaped segments identified as a, b, c, d, and the final partially-cylindrical uppermost portion of vertical stem 12, which is designated e. The lower edge of this offset portion 18 is stepped to coincide with the plurality of bulges provided in the sides thereof. The cylindrical segments, the lengths of the cylindrical segments, and the steps at the bottom of bulges or scallops of cylindrical segments a, b, c, and d provided in the exterior surface of the wedge-shaped portion 18 of insert 10, all correspond to the respective contours and depths of boreholes A, B, C, and D (See FIGS. 9 and 11–16) provided in the resected femoral head at the extended and flattened superior neck 15 thereof, into which these cylindrical segments a–d are respectively to fit, as indicated in FIG. 3.

As can be seen from FIGS. 5 and 6, the cross section of the insert 10 at line 5-5 of FIG. 3 shows recess or groove 16 and two inwardly-directed protuberances 28, resulting from overlapping circumferences d and e, which appear as convex arcuate bulges in the surface contour of offset portion 18 of insert 10.

From FIG. 6, which is a cross-section taken along line 6—6 at the extreme upper end of the insert 10, just below the proximal stem 22, as can be seen from FIG. 3, additional inwardly-extending protuberances 28 are apparent, resulting from the presence of a plurality of cylindrical segments a–e providing a plurality or series of overlapping circumferences, in this case five (5), which appear again as outwardly-extending or convex arcs or bulges a, b, c, d, in offset portion 18 and as convex surface e in the major vertical stem portion 12 of insert 10. All together, the body of the wedge-shaped or right-handed offset 18 comprises this series or plurality of overlapping cylindrical segments, thereby producing an elongated insert 10, as best shown in FIG. 9, having indentations on the exterior thereof, as shown in the form of scallops produced by overlapping circumferences, although more or less circumferences and indentations are equally adapted to provide an interlock with corresponding excavations in the resected superior neck 15 of the femoral head and may be employed for the same purpose. Although groove 16, as shown in FIGS. 4, 5, and 6, illustrates the presence of such a groove when the shaft 12 is tri-flanged and the groove in this position is continued up to the top of the insert, it will be understood that the cross sections will vary depending upon the number of flanges present in the shaft 12 and that the groove 16 in the cross section of FIG. 6 will not be present when the vertical stem 12 is flanged only further toward its bottom and not at its top. From FIG. 6 it will be apparent also that the circumference of cylindrical segment e is larger than of the other circumferential segments a–d, which will of course require corresponding circumferences of boreholes provided in the femoral head or the resected femoral head to receive the insert 10 with its vertical shaft 12 and its offset 18.

In FIG. 9 is shown how the elongated insert 10 of the invention, with its particular plurality of cylindrical segments, external contour and cross-section, and the aforementioned indentations or inwardly-extending protuberances, preferably in the form of scallops due to the aforesaid overlapping circumferences, fits snugly and securely into a corresponding elongated aperture 105 provided with locking or interlocking internal contours which prevent movement of the insert 10 within the aperture 105 provided therefor in the superior neck 15 of the femoral head. In this FIG. 9 the femoral cortex 1, the interior cancellous bone 3, the arcuate groove 16 in vertical shaft or stem 12, the upper planar surface 20 of the insert 10, the offset 18 of the insert 10, the proximal stem 22 of the insert 10 with its circular cross section 24 and the femoral cap or shell 26 press-fit thereto, are all visible.

FIG. 10 shows the upper portion of a femur 11 before resection of the femoral head, including the superior neck 15, the calcar or inferior neck 17, and the greater trochanter 13, with cuts for preferred resection of the femoral head for use in conjunction with a femoral insert 10 of the present invention being indicated by the shadow lines x, y, and z. Of course, in accord with the method of the invention, the first step can well be the resection of the femoral head although, as will be apparent to one skilled in the art from the following description of the method of the invention and the drilling fixture or jig 100 also provided according to the invention, it is not always necessary that the femoral head be resected prior to drilling of the same and, in some cases, as will also be apparent to one skilled in the art, the drilling may be effected advantageously prior to the resection. However, resection at least along the phantom line x, for extending and flattening of the superior neck and to provide a substantially planar surface thereto, is advantageously carried out prior to the drilling operation to provide a closer fit with drilling fixture 100, as shown in FIGS. 14–17, although resection along phantom lines y and z at this stage is optional and varies from case to case, it ordinarily not being advantageous or even necessary to effect the resection along the other two lines y and z shown in FIG. 10 prior to the drilling operation which will now be described. To repeat, in practice the resection of the femoral head prior to the drilling operation of the present invention preferably comprises resection of the upper surface of the femoral head to produce a resected superior neck surface defined by a plane extending through the natural head as shown in the upper horizontal phantom line "x" in FIG. 10, thereby producing a resected upper substantially planar surface in the resected femoral head for purposes of corresponding to the upper substantially planar surface 20 of the femoral insert 10, which in place will generally lie in the same plane as or somewhat above or below the planar surface of the resected femoral head, now having an extended and flattened superior neck 15, as shown in FIG. 1. The other cuts "y" and "z" shown in FIG. 10 are sometimes advantageously also made prior to the drilling operation but may, as already described, be postponed until after the drilling operation is completed, depending somewhat inter alia upon the condition of the bone.

In addition, it should be noted that, according to FIG. 17, when an allograft must be employed due to serious destruction or deterioration of the femoral head, the drilling operation may be at least partially carried out in advance on the bone section, synthetic or natural, which is to be grafted and/or secured in place in a much more seriously resected femur, as will be apparent from an inspection of FIG. 17 and as will be further discussed hereinafter.

Although the method of preparing the femoral head, especially a resected femur having an essentially-planar top surface, for insertion of the femoral insert 10 previously described, can be effected in any convenient manner, for example, simply by carrying out the steps of optionally resecting the femoral head to provide a substantially upper planar surface to the superior neck, providing an elongated excavation or aperture within the femoral shank generally corresponding to the shaft of a femoral insert to be inserted therein and essentially in line with the vertical axis of said femoral shank by drilling or routing of the same, providing an elongated aperture in said superior neck by drilling a plurality of cylindrical boreholes vertically downwardly into the superior neck between the end portion thereof distal to the femoral shaft and the portion thereof proximal to said femoral shaft, arranging said drilling to provide said boreholes with overlapping circumferences and thereby also to provide inwardly-extending protuberances at the intersections of said overlapping circumferences, extending said boreholes downwardly into said superior neck to different depths so as to bring them essentially into contact with or close proximity to the cortex of the femur at about the inferior neck and at progressively increasing depths beginning at the portion of the superior neck distal to said femoral shaft and progressing toward the portion proximal to said femoral shaft, thereby to provide an elongated excavation in said superior neck suitable for the close-fitting insertion of a femoral insert having essentially corresponding dimensions thereinto, a total of less than six (6) boreholes being preferred, one or more boreholes, e.g., the borehole provided proximally to said femoral shaft, possibly having a greater circumference than other boreholes provided in said superior neck, and the femoral insert having a corresponding contour and cross-section being thereafter press-fit therein without the aid of surgical cement.

In more detail, the method advantageously involves preparing an aperture in a femur for insertion of a complementarily-shaped femoral insert thereinto, comprising the steps of providing an elongated excavation or aperture within the femoral shaft generally corresponding to the shaft of a femoral insert to be inserted therein and essentially in line with the vertical axis of said femoral shaft by drilling or routing a borehole into the same, providing an elongated aperture in the superior neck of said femur by drilling a plurality of cylindrical boreholes vertically downwardly into the superior neck between the end portion thereof distal to the femoral shaft and the portion thereof proximal to said femoral shaft, arranging said drilling to provide said boreholes with overlapping circumferences and thereby also to provide inwardly-extending protuberances at the intersections of said overlapping circumferences, extending said boreholes downwardly into said superior neck to different depths so as to bring them essentially into contact with or close proximity to the cortex of the femur at about the inferior neck and at progressively greater depths beginning at the portion of the superior neck distal to said femoral shaft and progressing toward the portion proximal to said femoral shaft, thereby to provide an elongated excavation comprising a plurality of overlapping cylindrical boreholes in said superior neck suitable for the close-fitting insertion of a femoral insert having an essentially corresponding configuration thereinto.

Also, the method advantageously includes the step of resecting the femoral head to provide a substantially planar and extended surface to the superior neck, and the number of cylindrical boreholes drilled is advantageously less than six (6), and preferably a total of five (5) boreholes is drilled, usually five (5) cylindrical boreholes including a cylindrical borehole in the femoral shaft, and one cylindrical borehole may have a larger circumference than other boreholes, particularly the borehole drilled in said femoral shaft may have a greater circumference than other boreholes.

The femoral insert having complementary contour and cross-section is thereafter press-fit therein, and preferably a femoral insert having a substantially planar top surface and complementary contour and cross-section is thereafter press-fit therein without the aid of surgical cement. The method may advantageously be applied to a resected femur comprising an allograft secured in place therein or, conversely, the method may be applied to the femoral shaft of a resected femur and to an allograft comprising a superior neck, which allograft is thereafter secured in place in said femur.

The method of preparing the femoral head for insertion of the femoral insert 10 having corresponding dimensions is greatly facilitated by the employment of a drilling fixture or jig 100, as shown in FIGS. 11 through 16, which will now be more fully described.

Referring to FIG. 11, the drilling fixture or jig of the present invention is shown generally at 100. The body of the fixture is shown at 102, being generally rectangular in top plan view as well as from the side, and conveniently comprises a block of stainless steel or a lightweight metal such as aluminum or the like, which may be a cube, cuboid, a rectangular prism, or simply a block of rectangular cross section, but in any event advantageously having a relatively flat or planar bottom surface so as to lie in contact with or in close proximity to the superior surface of a femur to be drilled, especially the superior surface of a flattened and extended superior neck of a femur to be drilled.

Considering FIG. 11 along with partial sectional view 12, taken along the line 12—12 of FIG. 11, and the front view of FIG. 13, it will be seen that the body member 102 is mounted upon rod 110, which is preferably circular in cross section, which extends into and through aperture E in body member 102. Body member 102 is maintained in any desired vertical relation to rod 110 by adjusting and securing means, as shown threaded screw 118 with corresponding threads in block 102 and external adjusting knob 116. Preferably, body member 102 is also adjustable angularly or rotatively on rod 110 and, when rod 110 is circular in cross section to enable such angular adjustment, a flat portion 114 is advantageously provided for purposes of enabling rapid angular placement of body member 102 and releasable securement both vertically and angularly by the adjusting or clamping means just described. Rod 110 in turn surmounts elongated vertical shaft 112, having a vertical axis and corresponding generally to the vertical axis of a femoral shaft, the intramedullary cavity whereof it is designed to fill, once the intramedullary shaft of the femur has been excavated. As shown, vertical shaft 112 comprises a longitudinal arcuate groove, recess, or cavity 113 for purposes of enabling drilling to be carried out proximally to the rod 110 and shaft 112 without engaging any portion of shaft 112.

Support means for securing the fixture 100 to the top of a femoral head are advantageously provided in the form of downwardly angled arm member 120 and cross member 122, adapted to be positioned underneath and to engage the inferior neck of the femur upon which it is to be mounted in use. Angled support arm 120 is in turn secured to body member 102 by spacer or offset 119. In addition, cross member 122 advantageously comprises centering means 124 for centering the cross member 122, and hence the drilling fixture, with respect to the femoral head and/or flattened and extended superior neck of the femur being drilled, at approximately the calcar. As shown, the centering means is a groove or indentation with which the inferior portion of the femur at approximately the calcar or inferior neck is adapted to engage, or vice versa, and identified on cross member 122 as 124.

An essential aspect of the fixture 100 is the provision of an elongated opening 104 comprising a plurality of cylindrical vertically-arranged boreholes identified as A, B, C, and D therein. As will be noted, each of these boreholes A, B, C, and D is provided with a stop flange identified as A', B', C', and D' respectively, which stop flanges are progressively deeper, allowing progressively deeper drilling, in each of the bores from bore A, which is located distally from support rod 110 and shaft 113, until borehole D, which is proximal to rod 110 and shaft 112, and which accordingly permits the drill to drop deeper and drill further than the stop flange A' in the distal borehole A. Of course, the stop flange for borehole A need not be located within the borehole itself, but can as usual comprise the upper surface of fixture 100 adjacent to borehole A.

Also seen from FIGS. 11 and 12 are the lower bore wall LBW of borehole A, and all interior bore walls beneath stop flanges A', B', C', and D', the stop flanges A' through D' as shown being provided simply by reducing the diameter and circumference of the borehole as provided vertically in body member 102 from the top to the bottom thereof, thereby to provide a ledge or stop flange illustrated at A' through D'. As noted from FIG. 11, shaft 112 is surmounted by rod 110, and provision is made in body member 102 for passage of rod 110 through body member 102 by means of suitably-dimensioned aperture E which, as aforesaid, enables body member 102 to be mounted upon and to move vertically, and preferably also angularly, with respect to rod 110.

Figure 14:
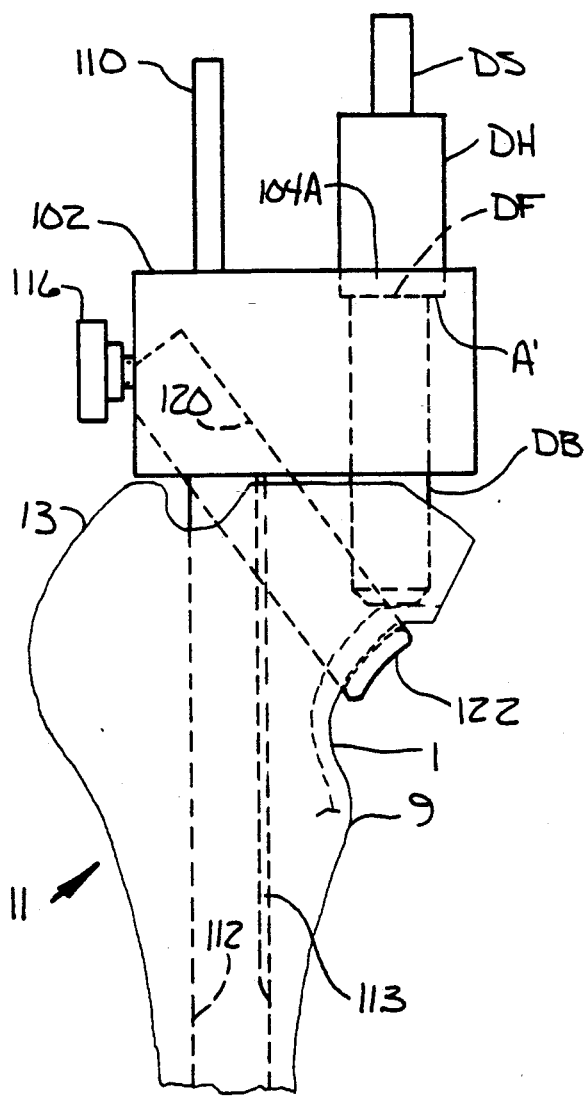
FIG. 14 is a side view depicting the drilling fixture in place atop the resected femoral head, having a substantially planar superior surface, with its vertical locator shaft member in place within the femoral shaft and with a first drill bit having drilled a cylindrical borehole into the femoral head all the way down to the cortex and having the flange of its drill head restrained from further penetration into the femoral head by a corresponding stop flange provided in the drilling fixture.
Figure 15:
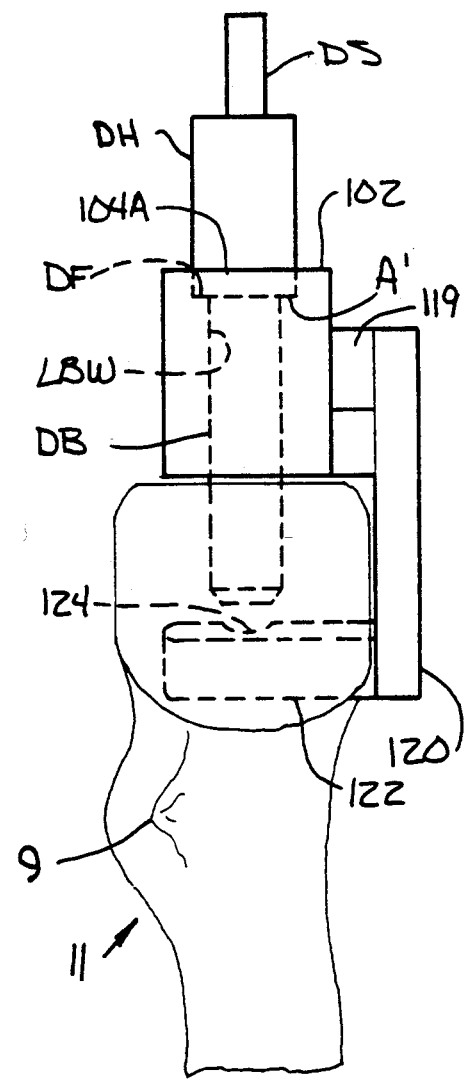
FIG. 15 is a front view of the assembly shown in FIG. 14.
Figures 16, 17:
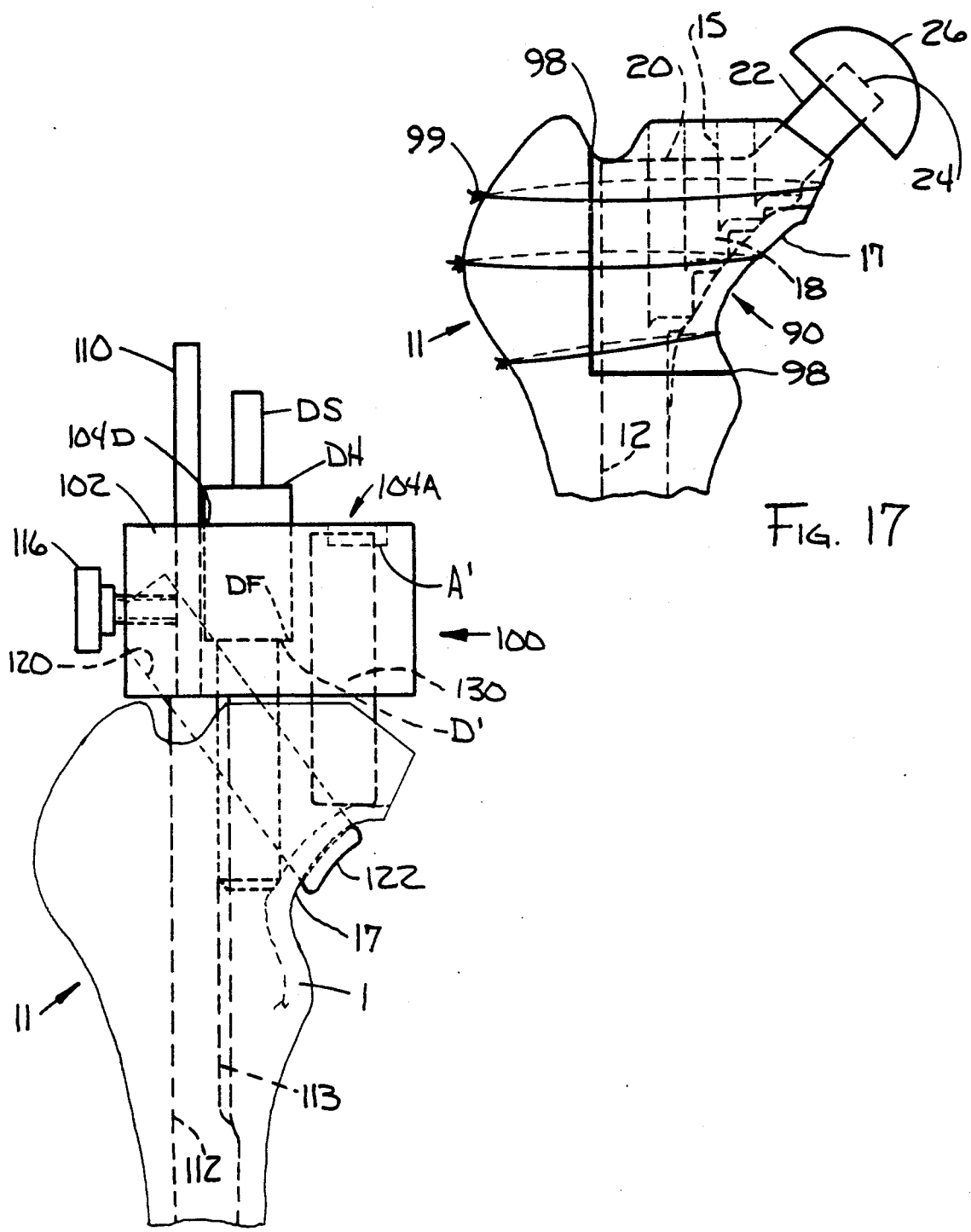
FIG. 16 is a side view like FIG. 14, showing a further cylindrical borehole drilled into the femoral head, the flange of the drill head resting upon the corresponding stop flange of the drilling fixture and the drill bit being shown as penetrating into the cancellous bone of the femur essentially all the way down to the cortex at approximately the calcar.
FIG. 17 shows an allograft, predrilled or drilled in place according to the present invention, wired into position as the top portion of a remodeled femur, with the femoral insert of the invention, including the femoral cap or shell affixed to its stem, secured in place in said allograft and having its vertical shaft portion firmly seated within the excavated interior of the femoral shaft or intramedullary canal.

Referring now to FIGS. 14 through 16, showing operation of the drilling fixture or rig 100 in practice, in FIG. 14 the drilling fixture or rig 100 is shown in place atop a resected femoral head having an essentially flat upper planar surface for its extended superior neck 15, secured in place therein by vertical shaft 112 in place in the excavated femoral shaft or intramedullary canal, with its concave surface or groove 113 facing the end of the drilling fixture body member 102 distal from rod 110, which is permanently affixed to the top of shaft 112 or integral therewith. The fixture 100 is also supported in place by downwardly-angled support arm 120 and crossmember 122, with centering groove 124 particularly apparent from FIG. 15. The cortex 1 of the femur 11 is shown inside of crossmember 122 and below drill bit DB, which is attached to drill head DH and then in turn to drill stem DS, drill head DH providing an outwardly-extending circumferential flange DF for engagement with and for resting upon stop flange A', which was already visible in FIG. 12. Only the borehole 104A most distal from shaft 112 and pin 110, and its associated drill means, are shown in FIGS. 14 and 15, for purposes of clarity and better illustration.

As seen from FIG. 16, however, when the first segment of elongated opening 104 in the form of borehole A has been drilled, a stabilizing plug 130 adapted to fit into the cylindrical boreholes may conveniently be inserted into the borehole A thus produced, further to stabilize, support, and position the drilling rig 100 upon the resected femoral head being drilled. All of the elements shown in the previous FIGS. 12–15 are apparent but, in addition, it is to be noted that the drill bit DB with its associated drill head DH and drill shaft DS have been moved into the position most proximal to rod 110 and shaft 112 for drilling of borehole D. As also seen, the reason for the preferred concavity 113 in vertical shaft 112 is apparent since the drill bit DB would otherwise encounter vertical shaft 112 during the course of drilling borehole D in the superior neck 15 of the femur down to the cortex 1 at approximately the calcar 17 where the drill bit engages or comes into close proximity to the cortex 1 of femur 11. The drill flange DF is again shown in contact with and resting upon the stop flange, in this case stopflange D' of body member 102, which stop flange D' is to be observed as being lower in body member 102 than stop flange A' and any additional stop flanges thereinbetween, that is, between borehole A, which is most distal from rod 110 and shaft 112, and borehole D, which is most proximal thereto.

Any number of circumferential boreholes such as A and D, including if desired A, B, C, and D, each with their own v stop-flange such as A', B', C', and D', may be imparted to the body member 102 of the drilling fixture or jig 100, to provide in the said drilling jig an elongated aperture 104, having any desired number of circumferentially-overlapping boreholes, thereby to produce an elongated excavation or aperture 104 with inwardly-extending protuberances at the intersections of the overlapping circumferences. Obviously, whatever the number of boreholes produced by drilling into the resected femur, the same number of circumferential cylindrical elements and dimensions must be provided in the offset 18 of femoral insert 10, so that the cross-section as well as the vertical lengths of the vertical shaft 12 and the cylindrical segments of wedge-shaped offset 18 correspond substantially exactly for a snug fit between the insert 10 and the elongated opening 104 provided in the resected femur to receive the same, and so that the insertion of the insert 10 into the aperture 104 can be effected conveniently, snugly, and preferably by press-fitting and without the need of medical cement, although medical cement may be employed by the surgeon to the extent the same may be required or desired to fill inadvertent gaps or points where contact is lost between the insert and the aperture provided for the same although, as will be apparent to one skilled in the art, according to the present invention, the manner of providing an aperture in the resected femoral head, and provision of the configuration and cross-section thereof as corresponding to the configuration and cross-section of the femoral insert itself, there is according to the present invention a greater likelihood of an exact fit between the insert and the aperture adapted to be filled by the insert, together with greater rigidity, permanence, and security against axial or rotational movement than with any femoral insert previously available to the medical profession. Once the insert is inserted, it is apparent that it is locked in place by the inwardly-extending protuberances in the aperture provided for the insert, corresponding to the outer surface and cross-section of the insert itself, so that cementing of the insert in place is really unnecessary inasmuch as the aperture provided in the remodeled femur and the insert can optimally be made to correspond exactly, so that a complete and secure press-fit is attainable using only a few well-placed blows with a surgical hammer. Alternatively, surgical cement can be used if deemed appropriate by the surgeon to provide increased stability, particularly against rotational forces. Of course, after the insert is in place in the resected femur, it is a simple matter to press-fit or otherwise secure the femoral cap or shell 26 upon the proximal stem 22, whatever may be the cross-section of the stem and the corresponding opening provided therefor in femoral cap or shell 26.

In FIG. 17 is shown a femur having a resected head and an essentially top planar surface on the extended superior neck, in this case, however, prepared by the use of a predrilled or drilled in place allograft. The allograft is shown in general at 90, secured by a plurality of wires 99 to femur 11 at the intersection 98—98 of the allograft and the femur proper. The vertical shaft 12 of the femoral insert 10 is shown in shadow lines inserted in the excavated intramedullary canal 5 of the femur, and the femoral insert 10 with its wedge-shaped offset 18 is shown in place in the resected femoral head, with all of the essential elements as described for previous Figures, albeit this time in place in an allograft which is in turn secured in a 90° angled resection 98—98 at the top of the femur.

In conclusion, from the foregoing, it is apparent that the present invention provides a novel femoral head replacement and reconstruction technique, involving minimum bone removal and maximal securement of the femoral insert in the resected femur, as well as a novel femoral insert itself for use therein, a novel method of providing or readying the femoral head for acceptance of the femoral insert of substantially corresponding identical configuration and dimensions to the elongated excavation made in the preferably flattened and extended superior neck of the femur, and a most convenient and advantageous drilling fixture or jig for use in the method, all having the foregoing enumerated characteristics and advantages. Perhaps most importantly, the prosthesis of the present invention provides maximal resistance against torsional or rotational loading.

It is to be understood that the invention is not to be limited to the exact details of construction, operation, or to the exact materials of construction, compositions, methods, procedures, or embodiments shown and described, as obvious modifications and equivalents will be apparent to one skilled in the art, and the invention is therefore to be limited only by the full scope which can be legally accorded the claims appended hereto.

I claim:

1. A femoral insert, adapted to be secured in a femoral shaft as part of a femoral hip joint replacement, comprising an elongated vertical shaft portion with a longitudinal axis generally corresponding to the vertical axis of a femoral shaft, and a wedge-shaped portion extending from the shaft portion at or near a top thereof and constituting an offset to the longitudinal axis of said vertical shaft, said wedge-shaped portion terminating in a stem portion adapted to be capped by a femoral cap or shell, said vertical shaft and offset wedge-shaped portions having a configuration, when viewed from the top of said insert, comprising a plurality of overlapping circles, with inwardly-extending indentations at the intersections of circumferences of the circles, side surfaces of said wedge-shaped-offset portion comprising a plurality of adjoining convexly-arcuate surface segments defining the exteriors of a plurality of vertically-arranged overlapping cylindrical segments, bottoms of which cylindrical segments are stepped due to being located at progressively greater distances from the top of said insert beginning adjacent said stem portion and progressing toward said vertical shaft portion.

2. A femoral insert of claim 1, wherein said insert is adapted to provide secure engagement within a correspondingly-shaped aperture in a resected femoral head and to provide contact or close proximity of the stepped bottom of said wedge-shaped portion with the cortex of said resected femoral head at the inferior neck thereof.

3. The femoral insert of claim 2, comprising also a femoral cap or shell in place on said stem.

4. The femoral insert of claim 1, wherein at least the bottom of said vertical shaft is flanged.

5. A femoral insert of claim 4, wherein said vertical shaft is multi-flanged.

6. A femoral insert of claim 5, wherein said vertical shaft is tri-flanged.

7. The insert of claim 6, wherein the vertical shaft is tri-flanged and an arcuate groove distal to the stem portion extends to the top of the shaft.

8. The insert of claim 1, wherein the number of cylindrical segments is less than six (6).

9. A femoral insert of claim 8, wherein said shaft and said wedge-shaped offset comprise five (5) cylindrical segments.

10. The insert of claim 8 having five (5), cylindrical segments including an at least partial cylindrical segment at the top of the vertical shaft.

11. The insert of claim 8, wherein one cylindrical segment has a larger circumference than other segments.

12. The insert of claim 1, having a top surface which is substantially planar.

13. The femoral insert of claim 1, adapted to be placed in a resected and correspondingly excavated femur.

14. The femoral insert of claim 2, adapted to be placed in a resected and correspondingly excavated femur.

15. The femoral insert of claim 2, adapted to be placed in a resected femur comprising a femur having an excavated femoral shaft and an allograft secured in place therein, said allograft having been pre-drilled to provide an aperture corresponding to a complementary configuration of the insert.

16. The femoral insert of claim 2, adapted to be placed in a resected femur comprising a femur having an excavated femoral shaft and an allograft secured in place therein, said allograft having been drilled-in-place to provide an aperture corresponding to a complementary configuration of the insert.

17. A method of preparing an aperture in a femur for insertion of a complementarily-shaped femoral insert thereinto, comprising the steps of providing an elongated excavation or aperture within the femoral shaft generally corresponding to the shaft of a femoral insert to be inserted therein and essentially in line with the vertical axis of said femoral shaft by drilling or routing a borehole into the same, providing an elongated aperture in the superior neck of said femur by drilling a plurality of cylindrical boreholes vertically downwardly into the superior neck between the end portion thereof distal to the femoral shaft and the portion thereof proximal to said femoral shaft, arranging said drilling to provide said boreholes with overlapping circumferences and thereby also to provide inwardly-extending protuberances at the intersections of said overlapping circumferences, extending said boreholes downwardly into said superior neck to different depths so as to bring them essentially into contact with or close proximity to the cortex of the femur at about the inferior neck and at progressively greater depths beginning at the portion of the superior neck distal to said femoral shaft and progressing toward the portion proximal to said femoral shaft, thereby to provide an elongated excavation comprising a plurality of overlapping cylindrical boreholes in said superior neck suitable for the close-fitting insertion of a femoral insert having an essentially corresponding configuration thereinto.

18. The method of claim 17, including the step of resecting the femoral head to provide a substantially planar and extended surface to the superior neck.

19. The method of claim 17, wherein the number of cylindrical boreholes drilled is less than six (6).

20. The method of claim 17, wherein a total of five (5) boreholes is provided.

21. The method of claim 17, wherein five (5) cylindrical boreholes are drilled including a cylindrical borehole in the femoral shaft.

22. The method of claim 17, wherein one cylindrical borehole has a larger circumference than other boreholes.

23. The method of claim 17, wherein the borehole drilled in said femoral shaft has a greater circumference than other boreholes.

24. The method of claim 17, wherein a femoral insert having complementary contour and cross-section is thereafter press-fit therein.

25. The method of claim 17, wherein a femoral insert having a substantially planar top surface and complementary contour and cross-section is thereafter press-fit therein without the aid of surgical cement.

26. The method of claim 17, when applied to a resected femur comprising an allograft secured in place therein.

27. The method of claim 17, when applied to the femoral shaft of a resected femur and to an allograft comprising a superior neck, which allograft is thereafter secured in place in said femur.

28. The method of claim 17, wherein the successive drillings are facilitated by the employment of a drilling fixture comprising elongated means adapted to fit into an excavated intramedullary canal of a femur and surmounted by mounting means, a body member mounted on said mounting means, means for adjusting said body member vertically and angularly upon said mounting means and for securing said body member in a predetermined position with respect to said mounting means and said femur, said body member comprising a plurality of boreholes, each with its respective stop means, adapted to cooperate with a drill bit comprising complementary stop means, for drilling cylindrical openings in the resected head of said femur to different depths, depending upon the position at which the stop means is located for a particular borehole provided in the body member of said fixture.

29. The method of claim 17, wherein the successive drillings are facilitated by the employment of a drilling fixture comprising an elongated vertical shaft adapted to fit into an excavated intramedullary canal of a femur and surmounted by a vertical rod, a body member mounted on said rod and adjustable vertically and angularly upon said rod and securable in a predetermined position on said rod, said body member comprising a plurality of boreholes, each with its respective stop flange, adapted to cooperate with a drill bit comprising a complementary flange, for drilling cylindrical openings in the resected head of said femur to different depths, depending upon the position at which the stop flange is located for a particular borehole provided in the body member of said fixture.

30. A drilling fixture or jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein, said boreholes comprising overlapping circumferences and each borehole being provided with stop means therefor, the said stop means for said plurality of boreholes being located at different heights for different boreholes, elongated means adapted to be inserted into an excavated femoral shaft, the position of said stop means, for said boreholes in said body member, being progressively vertically lower starting at a borehole which is distal to said elongated means and progressing toward a borehole which is proximal to said elongated means, and means for mounting and for releasably adjusting and securing said drilling fixture or jig both vertically and angularly atop the upper surface of the femur once said elongated means is in place in the borehole of said femoral shaft.

31. A drilling fixture or jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein, said boreholes comprising overlapping circumferences and each borehole being provided with a stop flange therefor, the said stop flanges for said plurality of boreholes being located at different heights for different boreholes, an elongated vertical shaft having a vertical axis, corresponding essentially to the vertical axis of a starting femoral shaft, having an elongated vertical borehole drilled therein, and adapted to be inserted thereinto, the position of said stop flanges, for said boreholes in said body member, being progressively vertically lower starting at a borehole which is distal to said vertical shaft and progressing toward a borehole which is proximal to said vertical shaft, and means for releasably adjusting and securing said drilling fixture or jig both vertically and angularly atop an upper surface of the femur once said elongated vertical shaft is in place in the borehole of said femoral shaft.

32. A drilling fixture of jig for use in the proper alignment of boreholes in a femur desired to be drilled to provide an aperture therein for insertion of a femoral insert having a configuration complementary to said aperture, comprising the following elements in combination:

a body member comprising a plurality of vertically-disposed boreholes therein, said boreholes comprising overlapping circumferences and each borehole being provided with a stop flange therefor, the said stop flanges for said plurality of boreholes being located at different heights for different boreholes, a separate vertical aperture in said body member which is spaced from said boreholes and adapted to receive mounting rod means therein, an elongated vertical shaft having a vertical axis corresponding essentially to the vertical axis of a femoral shaft having an elongated vertical borehole drilled therein, and adapted to be inserted thereinto, mounting rod means surmounting said vertical shaft and adapted to be inserted into said separate vertical aperture in said body member, securing means for adjusting the height of said body member upon said mounting rod means and maintaining it at a predetermined height thereon, the position of said stop flanges, for said boreholes in said body member, being progressively vertically lower starting at a borehole which is distal to said mounting rod means and progressing toward a borehole which is proximal to said mounting rod means, and further releasable securement means for releasably securing said drilling fixture or jig in place atop an upper surface of a femur once said elongated vertical shaft is in place in the borehole of said femoral shaft and said body member is in place and releasably secured on said mounting rod means.

33. The drilling fixture of claim 32, wherein said body member is also rotatable on said mounting rod means.

34. The drilling fixture of claim 32, wherein said securing means comprises threaded screw means and corresponding threads in said body member.

35. The drilling fixture of claim 32, wherein said mounting rod means comprises a flat portion for engagement by said screw means to minimize undesired rotation thereof and to assist in fixing said body member at a proper angle both with respect to said mounting rod means and with respect to the femur being drilled.

36. The drilling fixture of claim 32, wherein said elongated vertical shaft has an arcuate recess or groove along the length thereof facing the borehole in said body member most proximal thereto for enabling a drill bit to be placed in said proximal borehole without engaging said shaft.

37. The drilling fixture of claim 32, wherein said further releasable securement means comprises an arm attached to said body member at an angle and a cross member adapted to engage the outer surface of a femur being drilled at about the inferior neck thereof.

38. The drilling fixture of claim 32, comprising also a drill bit having a drill stem and a drill head, said drill head providing a flange for engagement with said stop flanges, provided for said boreholes in said body member, and having a drill bit length below said drill head flange which is calculated to permit said drill bit to drill into the superior neck of the femur being drilled to a point in contact with or closely adjacent to the cortex of the femur at about the inferior neck thereof.

39. The drilling fixture of claim 38, including a stabilizing plug for insertion into a first borehole in said femur, once it has been completed, through the corresponding borehole provided in said body member of said drilling fixture to further stabilize the drilling fixture upon the femur.

40. The drilling fixture of claim 32, wherein said body member has a substantially planar lower surface for lying flat in contact with or in close proximity to a substantially planar superior surface of a flattened and extended superior neck of a femur being drilled.

* * * * *